(12) United States Patent
Larsen

(10) Patent No.: US 10,222,249 B2
(45) Date of Patent: Mar. 5, 2019

(54) LIQUID LEVEL SENSING AND DIAGNOSTIC DETERMINATION

(71) Applicant: GM GLOBAL TECHNOLOGY OPERATIONS LLC, Detroit, MI (US)

(72) Inventor: John F. Larsen, Campbellcroft (CA)

(73) Assignee: GM Global Technology Operations LLC, Detroit, MI (US)

( * ) Notice: Subject to any disclaimer, the term of this patent is extended or adjusted under 35 U.S.C. 154(b) by 144 days.

(21) Appl. No.: 15/584,514

(22) Filed: May 2, 2017

(65) Prior Publication Data
US 2018/0321071 A1   Nov. 8, 2018

(51) Int. Cl.
*G01F 23/00* (2006.01)
*G01F 23/22* (2006.01)
*G01N 35/10* (2006.01)
*G05D 9/12* (2006.01)
*G06Q 10/06* (2012.01)

(52) U.S. Cl.
CPC .......... *G01F 23/0069* (2013.01); *G01F 23/22* (2013.01); *G01N 35/1009* (2013.01); *G05D 9/12* (2013.01); *G06Q 10/0631* (2013.01)

(58) Field of Classification Search
CPC ...... G01F 23/38; G01F 23/266; G01F 23/268; G01F 23/263; G01F 23/26; G01F 23/265; G01F 23/363; G01F 23/32; G01F 23/72; G01F 23/36; G01F 23/0007; G01F 23/0076; G01F 23/24; G01F 23/284; G01F 25/0061; G01F 23/0061; G01F 23/0069; G01F 23/296; G01F 23/2962; G01F 23/62; G01F 22/00; G01F 23/18; G01F 23/22; G01F 23/34; G01F 23/02; G01F 23/14; G01F 23/243; G01F 23/246; G01F 23/247; G01F 23/248; G01F 23/2845; G01F 23/292; G01F 23/74; G01F 23/0046; G01F 23/20; G01F 23/2921; G01F 23/2963; G01F 23/303; G01F 23/76; G01F 15/003; G01F 1/661; G01F 1/6847; G01F 1/69; G01F 23/00; G01F 23/0038; G01F 23/162; G01F 23/185; G01F 23/226; G01F 23/241; G01F 23/242; G01F 23/244; G01F 23/261; G01F 23/2922; G01F 23/2927; G01F 23/2928; G01F 23/2961; G01F 23/366; G01F 23/40; G01F 23/54; G01F 23/543; G01F 23/60; G01F 23/606; G01F 23/64; G01F 23/683
See application file for complete search history.

(56) References Cited

U.S. PATENT DOCUMENTS

| 8,646,328 | B2 * | 2/2014 | Knowles | G01F 23/2961 73/290 V |
| 2005/0279855 | A1 * | 12/2005 | Baker | G01F 23/266 239/71 |
| 2014/0260576 | A1 * | 9/2014 | Sweppy | G01F 23/32 73/114.54 |

* cited by examiner

*Primary Examiner* — Andre J Allen
(74) *Attorney, Agent, or Firm* — Quinn IP Law

(57) ABSTRACT

A method for determining a liquid level of a reservoir includes sensing a plurality of liquid level points during a plurality of defined computation intervals, and determining filtered block points from the sensed liquid level points occurring during each of the computation intervals. The method fits a regression model to the determined filtered block points, including determining a slope and a standard error of regression, and determines an actual liquid level change from the slope of the regression model. The method may also include making a diagnostic determination if the method determines that a confidence ratio is sufficiently high.

16 Claims, 5 Drawing Sheets ns affected by, or influencing, liquid level shown in FIG. 3, illustrating a calculation and interpretation portion or block of the method.
LIQUID LEVEL SENSING AND DIAGNOSTIC DETERMINATION

INTRODUCTION

This disclosure generally relates to sensing and determination of liquid level, and to diagnosis of liquid level sensors and other components or systems affected by, or influencing, liquid levels of a reservoir mounted to a moving platform.

SUMMARY

A method for determining a liquid level in a reservoir subject to disturbances and diagnosing components thereof is provided. The method includes sensing a plurality of liquid level points during a plurality of defined computation intervals, and determining a plurality of filtered block points from the sensed liquid level points occurring during each of the computation intervals. The method fits a regression model to the determined filtered block points, including determining a slope and a standard error of regression, and determines an estimate for the actual liquid level change from the slope of the regression model.

The method may also include monitoring an inflow and an outflow from the reservoir, determining an expected liquid level change from the inflow and the outflow, and calculating a potential level error from the difference between the expected liquid level change and the actual liquid level change.

The method also determines a confidence ratio from the standard error of regression of the regression model, and compares the confidence ratio to a minimum confidence ratio. If the determined confidence ratio is higher than the minimum confidence ratio, the method will make a diagnostic determination from the potential level error. However, if the determined confidence ratio is not higher than the minimum confidence ratio, the method will not make a diagnostic determination, irrespective of the potential level error.

The above features and advantages, and other features and advantages, of the present subject matter are readily apparent from the following detailed description of some of the best modes and other embodiments for carrying out the disclosed structures, methods, or both.

DETAILED DESCRIPTION

Figure 1:
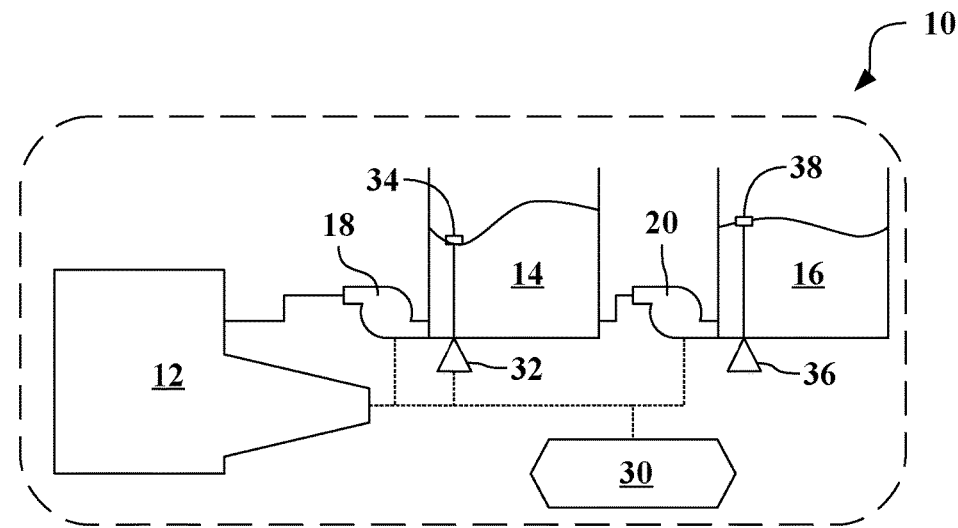
FIG. 1 is a schematic diagram of a multi-tank liquid system for a vehicle.

In the drawings, like reference numbers correspond to like or similar components whenever possible throughout the several figures. There is shown in FIG. 1 a schematic, diagrammatic view of a vehicle 10 having a powertrain 12. In general, the powertrain 12 provides motive energy for the vehicle 10, and may be configured as a conventional or hybrid powertrain.

A primary reservoir 14 holds a fluctuating amount of liquid. The primary reservoir 14 may also be referred to as the reservoir of interest. Liquid, such as fuel, may be added to, or withdrawn from, the primary reservoir 14 for operation of the powertrain 12.

While the present disclosure may be described with respect to specific applications or industries, those skilled in the art will recognize the broader applicability of the disclosure. Those having ordinary skill in the art will recognize that terms such as "above," "below," "upward," "downward," et cetera, are used descriptively of the figures, and do not represent limitations on the scope of the disclosure, as defined by the appended claims. Any numerical designations, such as "first" or "second" are illustrative only and are not intended to limit the scope of the disclosure in any way.

Features shown in one figure may be combined with, substituted for, or modified by, features shown in any of the figures. Unless stated otherwise, no features, elements, or limitations are mutually exclusive of any other features, elements, or limitations. Furthermore, no features, elements, or limitations are absolutely required for operation. Any specific configurations shown in the figures are illustrative only and the specific configurations shown are not limiting of the claims or the description.

The associated vehicle, and any components incorporated therewith, may be representative of numerous types of vehicles, including planes, trains, automobiles, or any other rolling or movable platform. Additionally, heavy industrial, construction, and mining equipment may incorporate features of the methods or algorithms described herein.

In addition to the primary reservoir 14, the vehicle 10 includes an optional secondary reservoir 16. The secondary reservoir 16 may be used to store additional liquid, such as fuel, that is periodically transferred to the primary reservoir 14. For example, in larger industrial, commercial, or other heavy-duty vehicles, double tank systems may be used to extend operating time between stops for refueling.

A primary pump 18 transfers liquid from the primary reservoir 14 to the powertrain 12. The vehicle 10 illustrated also includes a transfer pump 20, which transfers liquid from the secondary reservoir 16 to the primary reservoir 14.

The methods and algorithms described herein may be used to improve the diagnosis, for proper function, of components and systems affected by, or influencing, the level of liquids, such as fuel, in the primary reservoir 14, the secondary reservoir 16, additional reservoirs, or combinations thereof. In particular, where the vehicle 10 is subject to directional disturbances such as acceleration, braking, cornering, or changes in road gradient, the level of liquids within the reservoirs may be difficult to accurately measure due to physical movement and jostling of the liquids. Furthermore, removal of liquid from, or addition of liquid to, any specific reservoir may complicate this assessment.

While much of the description herein focuses on liquid fuel as the liquid of interest, other liquids may also be used with the methods, systems, and algorithms described herein. For example, and without limitation, the methods may be applied to: transmission fluid, coolant, or diesel exhaust additives.

A control system 30 is in communication with components of the vehicle 10. The control system 30 includes sufficient processing, memory, and storage capability to receive inputs, perform calculations, and send outputs related to executing the methods described herein. The control system 30 also has sufficient capabilities to control any necessary components, and sense or estimate additional parameters, related to executing the methods described herein.

At least one sensor is incorporated into the systems of the vehicle 10, and is in communication with at least the control system 30. In many configurations, systems of the vehicle 10 incorporate at least one liquid level sensor for each liquid reservoir, particularly those related to executing the methods described herein. For example, a primary sensor 32 provides readings of the level of liquid within the primary reservoir 14, such as through communication with a float 34 and the control system 30. These readings may be output as, for example and without limitation, voltage or position within the primary reservoir 14.

The output from the primary sensor 32 is used by the control system 30 as an instantaneous reading of the level of liquid within the primary reservoir 14. However, as the liquid moves within the primary reservoir 14 due to movement of the vehicle 10, these instantaneous readings or data points may not be representative of the actual bulk level of liquid within the primary reservoir 14.

The structures of FIG. 1 are basic illustrations, and are shown only to represent some of the components that may be associated with the methods, algorithms, or techniques described herein. In many configurations of the vehicle 10, the secondary reservoir 16 may also have a sensor system detecting liquid levels therein, such as a secondary sensor 36 in communication with a float 38.

Figure 2:
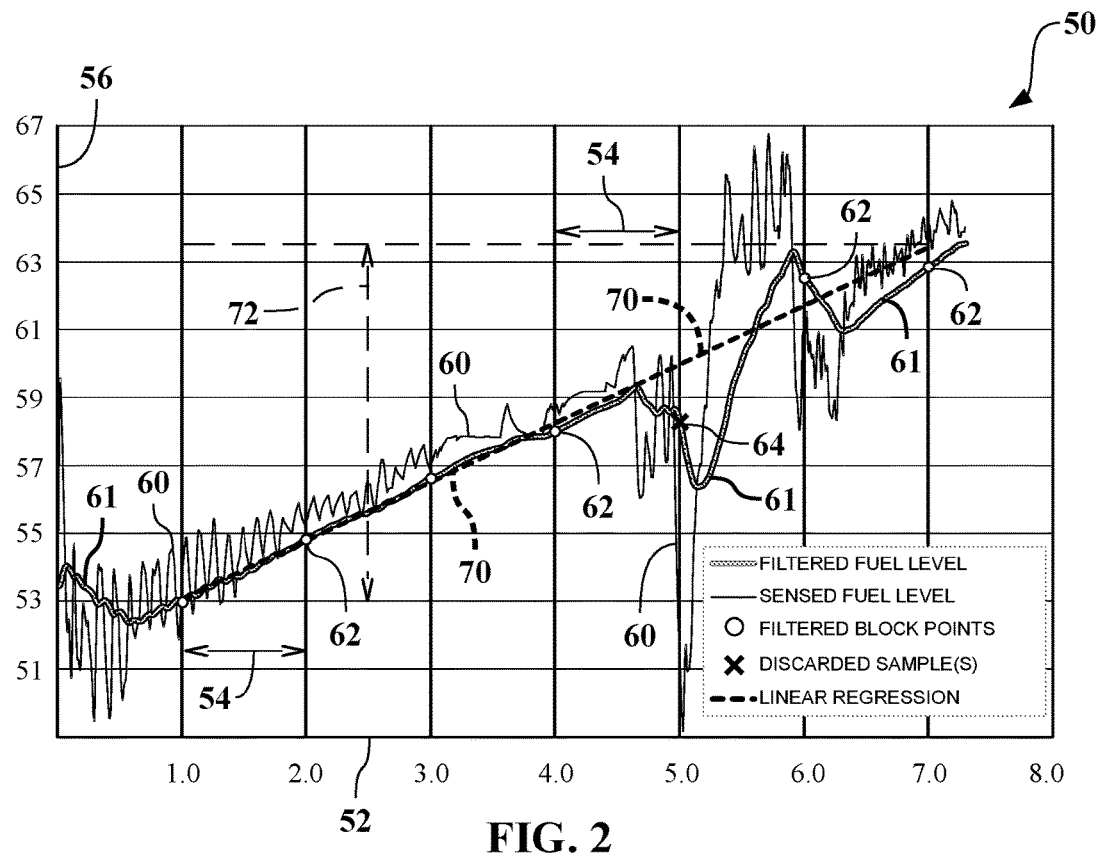
FIG. 2 is a schematic graphical illustration of data collection and processing of liquid level data for the purpose of diagnosing, for proper function, components and systems affected by, or influencing, liquid level, for a system such as that shown in FIG. 1.

Referring to FIG. 2, and with continued reference to FIG. 1, there is shown a graph 50 illustrating data collection and processing by systems similar to those shown in FIG. 1. An x-axis 52 represents the progression of measurement intervals, such as time, expected quantity of liquid transferred, expected change in liquid level, or any other quantity that is proportional to actual change in liquid level within the reservoir of interest. In the example illustrated, the x-axis 52 is the expected change in liquid level within the reservoir of interest.

Each unit of the x-axis 52 may also correspond to a computation block or computation interval 54. For example, and without limitation, in the graph 50 each computation block or computation interval 54 represents one liter of expected change in a liquid reservoir, such as the primary reservoir 14. The level changes, for example and without limitation, based on expected liquid inflows, such as due to operation of the transfer pump 20, and outflows, such as operation of the primary pump 18. The size of the computation interval 54 is chosen through calibration in a manner so as to ensure that a requisite number of regression samples are collected within a monitoring period.

Therefore, the values of the x-axis 52 may also be referred to as expected fuel transfer or expected liquid level change. A y-axis 56 represents measured or sensed liquid level, which may be in engineering units, such as liters or kilograms or millimeters, within the liquid reservoir of interest. In the example shown in FIG. 2, the units of both the x-axis 52 and the y-axis 56 are liters (L).

A sensed level 60 shows readings of unfiltered sensed liquid level within the reservoir of interest from a sensor, such as the primary sensor 32 reading data from the primary reservoir 14 shown in FIG. 1. The sensed level 60 may be formed from numerous data points, or may be an analog signal that can be converted into individual data points. The chart 50 also illustrates a filtered liquid level, or simply filtered level 61, which may be, for example and without limitation, an arithmetic mean or an exponentially weighted moving average of the data points in the sensed level 60.

As shown by the sensed level 60, sloshing or jostling of liquid within the primary reservoir 14 cause readings from the primary sensor 32 to vary greatly. The period of operation displayed in the chart 50 may be indicative of the vehicle 10 accelerating, decelerating, cornering, moving over hills, road variances (potholes, bumps, et cetera), or all of the aforementioned.

A plurality of computation points, filtered block levels, or filtered block points 62 represent a processed compilation of values of all the sensed liquid level points during each computation interval 54. Therefore, each filtered block point 62 is a mathematically filtered representation of the data points occurring during each respective computation interval 54. As illustrated in FIG. 2, the filtered block points 62 may be determined from the exponentially weighted moving average of the data points in the sensed level 60 over each computation interval 54, such that the filtered block points 62 occur along the filtered level 61. The methods described herein may also include techniques to identify and discard outlying computation points, such as an outlier point 64.

A regression line 70 represents a statistical curve-fit of the filtered block points 62. Note that while the regression line 70 is illustrated as a single, linear curve, it may also be a non-linear curve, or a collection of shorter, linear vectors. For example, and without limitation, the regression line 70 may be developed via ordinary least squares (OLS) or polynomial regression. An actual level change 72 is determined from the regression line 70, and represents an estimated actual change in level of the liquid within the reservoir of interest, such as the primary reservoir 14, over the observation window shown in FIG. 2.

Note that the values shown in FIG. 2 are exemplary only. The data illustrated may not be representative of an actual situation or test occurring on any vehicle.

Referring also to FIGS. 3-6, and with continued reference to FIGS. 1 and 2, there is shown an illustrative flow chart for an algorithm, system, or method 100 for diagnosing, for proper function, components and systems affected by, or influencing, a liquid level, and for determining the liquid level, of a liquid tank or tanks, such as the primary reservoir 14 within the vehicle 10 shown in FIG. 1. The method 100 shown in FIGS. 3-6 illustrates some of the inputs, outputs, and techniques shown in FIG. 2.

Figure 3:
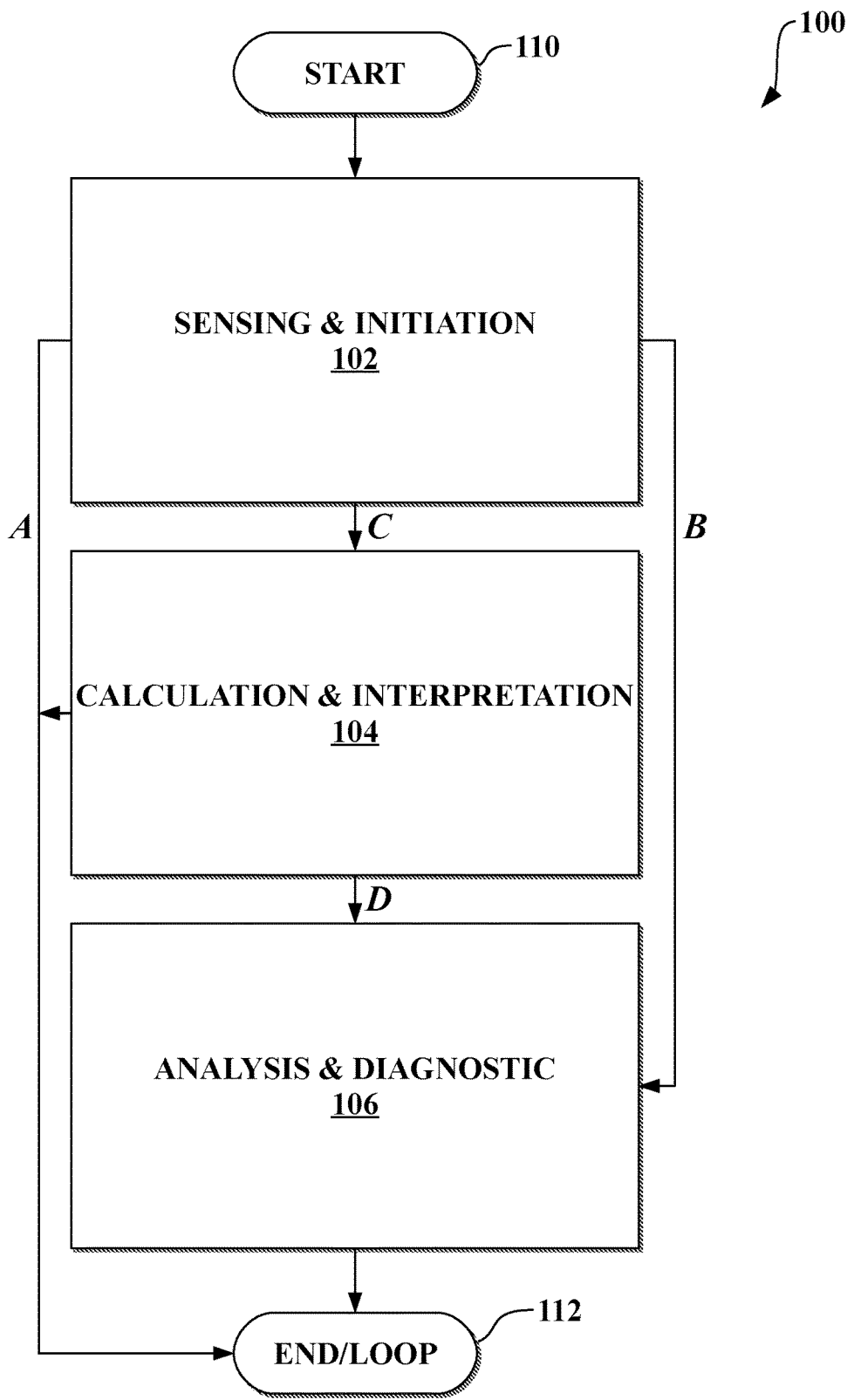
FIG. 3 is a schematic flow chart illustrating a high-level layout of a method for diagnosing, for proper function, components and systems affected by, or influencing, liquid level, for systems and for determining a liquid level of a liquid reservoir or reservoirs, such as those shown in FIG. 1, subject to data capture and analysis, such as that shown in FIG. 2.

FIG. 3 shows a high-level layout of the method 100, and illustrates the interactions between three sub-portions or blocks. A first block 102 may be referred to as a sensing and initiation block, and is illustrated in greater detail in FIG. 4. A second block 104 may be referred to as a calculation and interpretation block, and is illustrated in greater detail in FIG. 5. A third block 106 may be referred to as an analysis and diagnostic block, and is illustrated in greater detail in FIG. 6.

The method 100 may be beneficial for improving functional diagnosis of components and systems affected by, or influencing, liquid level of the primary reservoir 14 when the vehicle 10 is subject to movement causing movement of the liquid within the primary reservoir 14. Otherwise, movement of liquid within the primary reservoir 14 may lead the control system 30 to incorrectly diagnose the functional performance of components or systems affected by, or influencing, liquid level, such as the primary sensor 32 or transfer pump 20. Disturbances that can influence liquid level sensing include, without limitation: bumpy roads, erratic or abrupt driving maneuvers and instances of lateral or longitudinal acceleration (e.g., cornering, acceleration, deceleration, changes in road gradient).

The order and procession of steps within the method 100 is illustrative of only one configuration for executing and performing the processes, methods, and algorithms described herein. Steps may be reordered or combined, depending on specific configurations and implementation in specific vehicles or systems. Connections between the blocks maybe shown with either letters or numbers, and some steps or portions may be shown in more than one block.

FIG. 3 shows the general flow patterns and interconnections between the blocks. However, more illustrative progressions and pathways are illustrated in the more-detailed views of FIGS. 4-6. While the method 100 may be illustrated or described with reference to the vehicle 10 of FIG. 1, the data shown in FIG. 2, or both, these diagrams are not limiting of the method 100 or the structures and techniques to which the method 100 may be applied. The sub-portions or blocks are bookended by a start or initialization step 110 and an end or loop step 112, which may also be considered portions of the first block 102 and the third block 106, respectively.

Step 110: Start/Initiation.

The method 100 may begin at a start or initialization step, during which time the method 100 is made active and may be monitoring, or even controlling, portions of the vehicle 10, the powertrain 12, or both. Initiation may occur, for example, in response to the operator inserting the ignition key or in response to specific conditions being met, such as whenever the control system makes the powertrain 12 operational. The method 100 may be running constantly or looping constantly whenever the vehicle is in use, or may be configured to operate at predetermined intervals.

In some configurations of the method 100, the primary sensor 32 outputs a liquid level point at each occurrence of the start step 110 which will be used throughout the remainder of the method 100. For example, with reference to FIG. 2, many sensed liquid level points, or simply data points, form the sensed level 60. At least some of the liquid level points are stored and used by the control system 30.

The liquid level points may refer to any quantifiable measurement relating to the amount of liquid in the primary reservoir 14. For example, and without limitation, the liquid level may be expressed as volume or mass, or even as position or distance—relating to a linear position of the sensor within the reservoir, which may be directly or indirectly related to volume or mass. Furthermore, the control system may determine the liquid level based on different signal outputs from the sensor, such as voltage.

Step 112: End/Loop.

Ending the method 100 may include deactivating the method 100 until called upon for another specific occurrence. Alternatively, the method 100 may be looping or running continuously until other conditions are met, such as the vehicle 10 being deactivated or placed into a power-saving mode. The method 100 may be part of a larger vehicle control system and may be a sub-process of other control or diagnostic algorithms. As shown in the figures, some of the sub-portions or blocks include paths or escapes directly to the end step 112.

Figure 4:
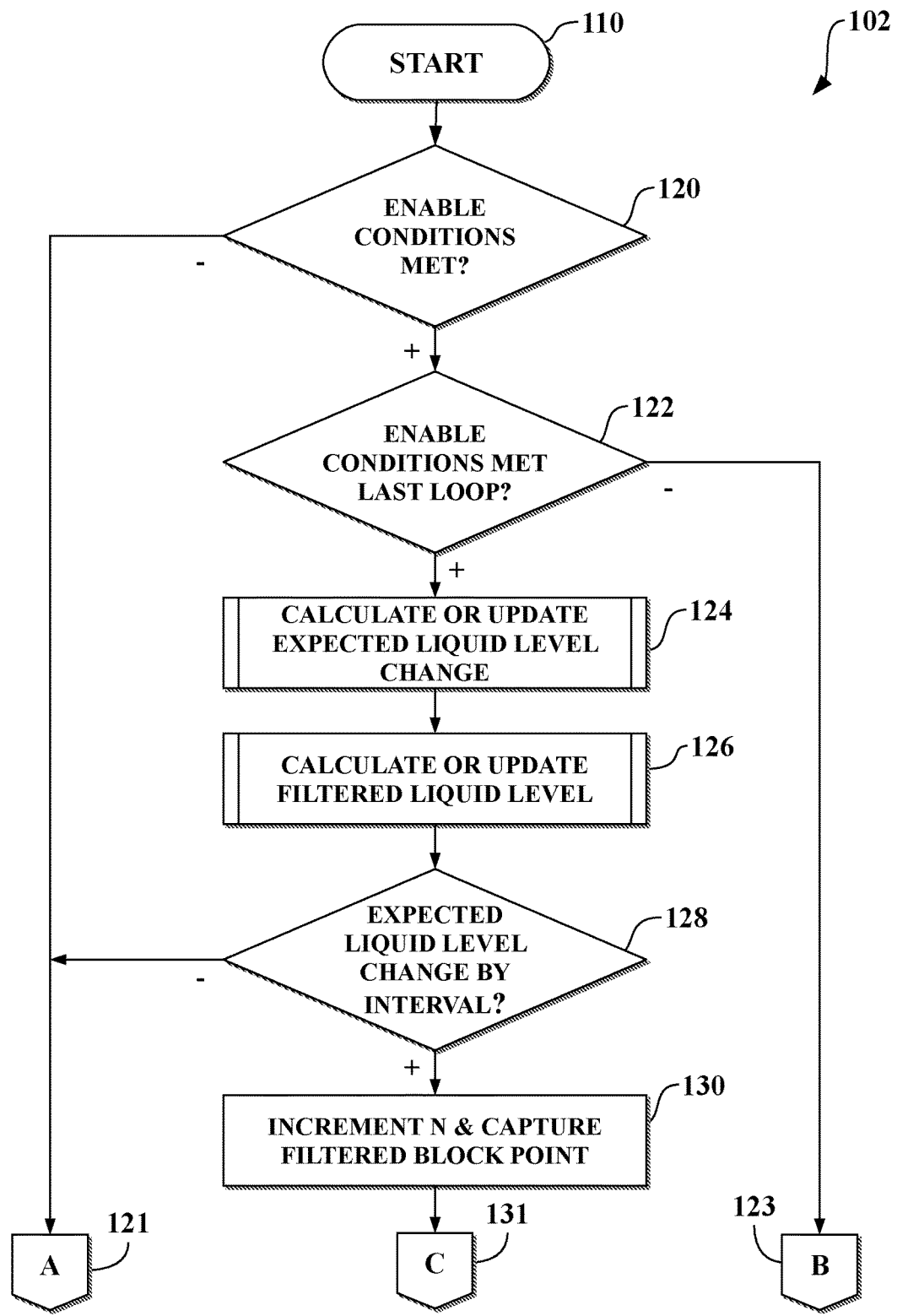
FIG. 4 is a schematic detail flow chart of a portion of the method for diagnosing, for proper function, components and systems affected by, or influencing, liquid level shown in FIG. 3, illustrating a sensing and initiation portion or block of the method.
Figure 5:
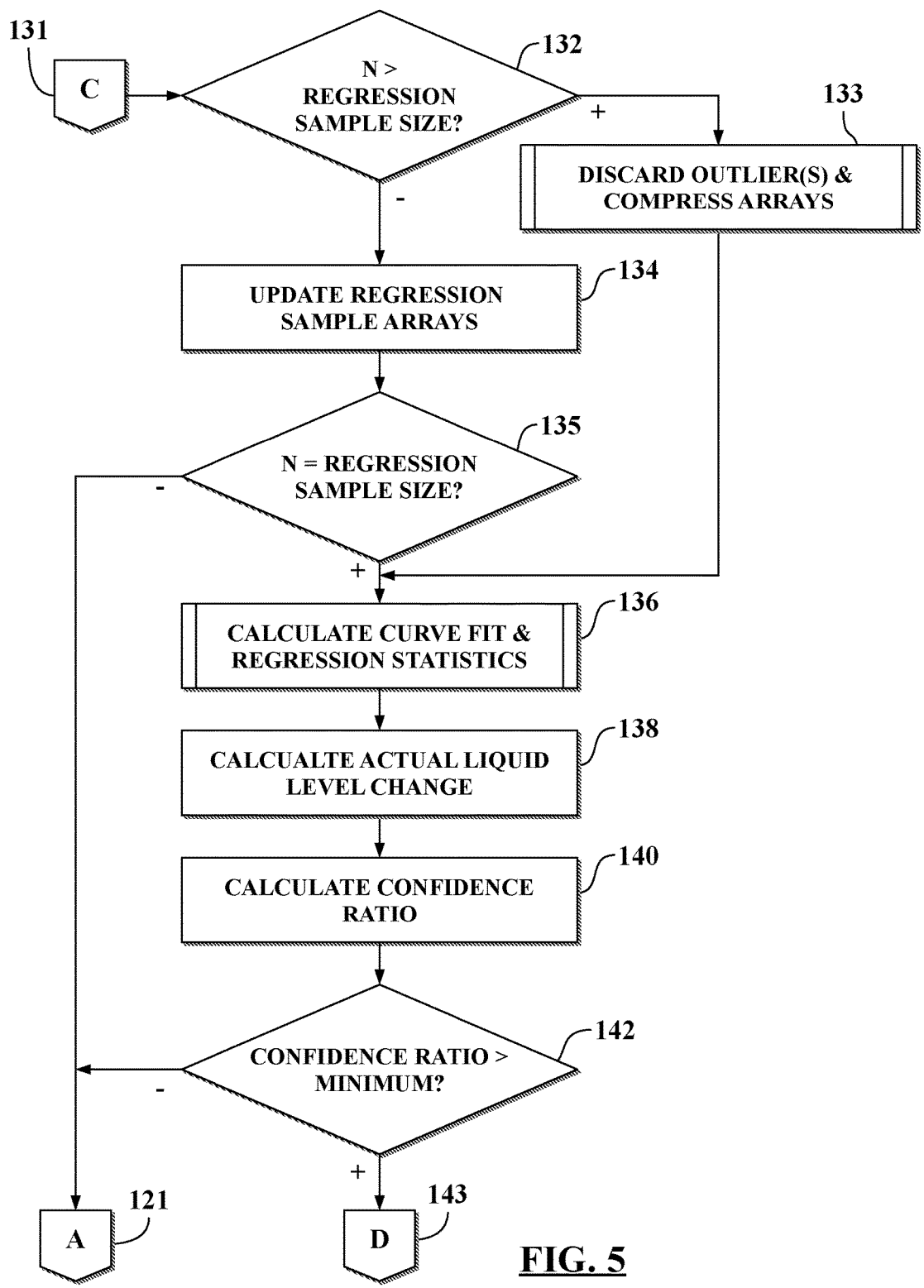
FIG. 5 is a schematic detail flow chart of another portion of the method for diagnosing, for proper function, components and systems affected by, or influencing, liquid level shown in FIG. 3, illustrating a calculation and interpretation portion or block of the method.

Referring to the detailed view of the first block 102, as shown in FIG. 4, the steps involve raw sensing and filtering of liquid levels. Additionally, the first block 102 verifies that conditions are suitable for the remainder of the method 100. Note that, as used in the flowcharts, decision steps proceed via "+" for yes or positive determinations, and via "−" for no or negative determinations.

After the end step 112, the method 100 likely loops at prescribed intervals. The method 100 may loop based on lapse of time, such as every 100 milliseconds, or some other triggering event, such as every 0.1 liters of fuel consumed by the powertrain 12.

Step 120: Enable Conditions Met?

The method 100 determines whether diagnostic enable criteria are satisfied. These conditions are specific to the vehicle 10 and the control system 30 incorporated therewith. For example, and without limitation, the method 100 may verify that: input signals are valid, no intervening actions have occurred that affect diagnostic reliability, and that related systems are operational. One of the input signals that may be checked before enabling the method 100 is whether the primary sensor 32 is outputting a sensed liquid level point. If the enable conditions are not met, the method 100 proceeds to the end step 112, and may loop immediately or after a predetermined pause.

Step 122: Enable Conditions Met Last Loop?

When the enable conditions are met on the current loop, but were not met on the immediately prior loop, the method 100 needs to initialize the diagnostic status. The current loop, and any characteristics thereof, may be referred to as loop "n", such that the last loop is "n−1" and the next loop is "n+1".

The value of n may also be the number of samples taken, or liquid level points reported, by the primary sensor 32 and read or used by the control system 30 in the method 100. In such a configuration, each loop of the method 100 corresponds to one sampled liquid level point from the primary sensor 32. However, other configurations of the method 100 may utilize multiple liquid level points, such as five or ten points, for the calculations and determinations in each loop.

Figure 6:
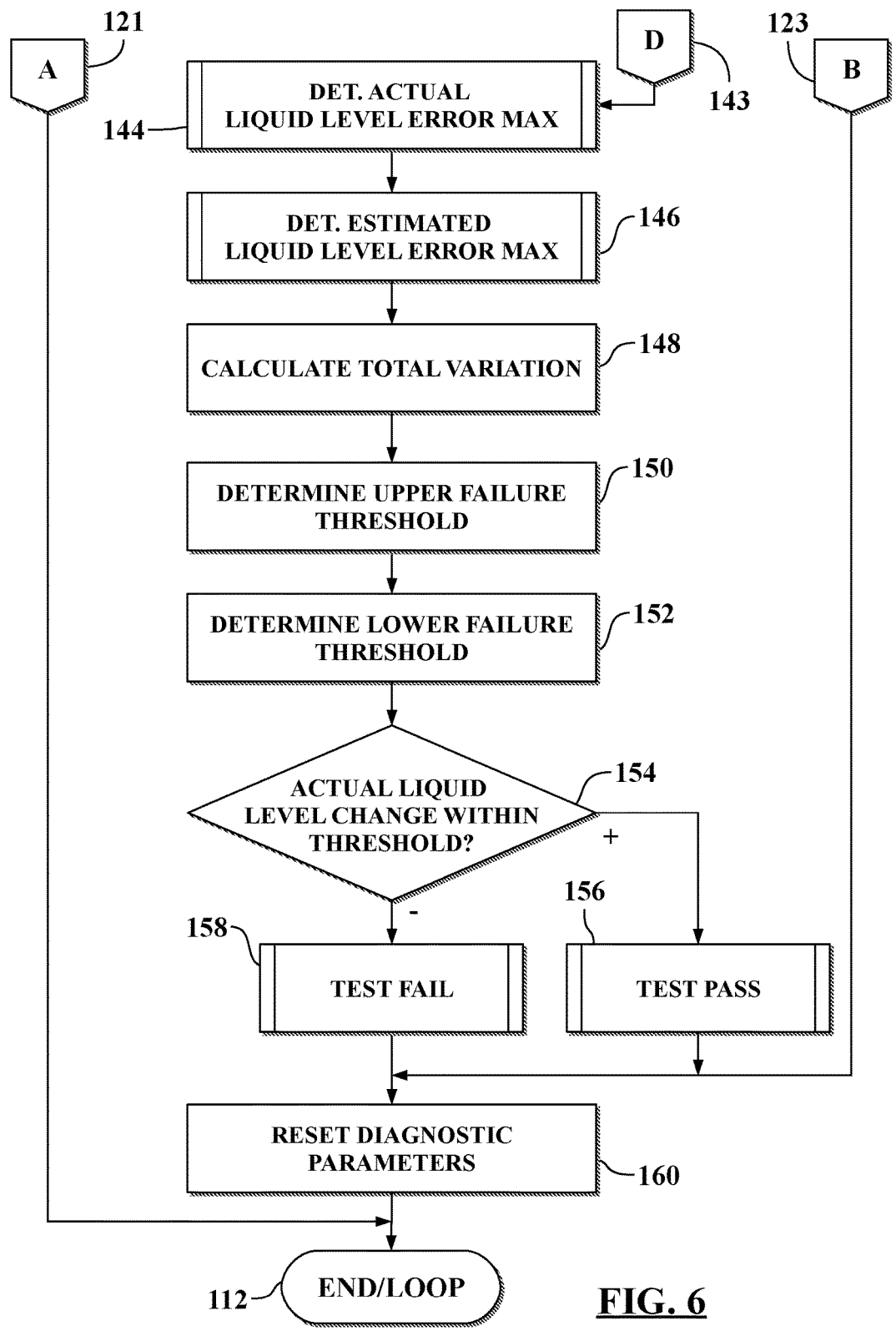
FIG. 6 is a schematic detail flow chart of another portion of the method for diagnosing, for proper function, components and systems affected by, or influencing, liquid level shown in FIG. 3, illustrating an analysis and diagnostic portion or block of the method.

If the enable conditions were not met on the prior loop, the method 100 proceeds to reset itself, which is shown at step 160 in FIG. 6. As described herein, the reset step 160 includes zeroing the expected liquid level change and the value of "N", which is the number of filtered block points captured, both of which are described in more detail herein.

Step 124: Calculate or Update Expected Liquid Level Change.

The method 100 determines or calculates an expected liquid level change, which represents the change in liquid level that is expected to occur. The control system 30 is monitoring an inflow and an outflow from the primary reservoir 14, such as by monitoring expected operation of the primary pump 18 and the transfer pump 20. Therefore, the method 100 determines either the expected liquid level (as a total calculation) or the expected liquid level change, which may be used to update the total expected liquid level, from the monitored inflow and the outflow.

For example, and without limitation, the expected liquid level change may be determined by integrating flows in and out of the primary reservoir 14 with respect to time. Factors contributing to the expected liquid level change include, depending on the liquid and without limitation: fuel consumed by the powertrain 12, liquid transferred to the primary reservoir 14 by the transfer pump 20, and diesel exhaust fluid (DEF) injected.

For example, the control system 30 may determine that, over a predefined period, or relative to the prior loop, the powertrain 12 was expected to consume 0.1 liters of fuel from the primary reservoir 14 and the transfer pump 20 was expected to transfer 0.2 liters to the primary reservoir 14. Therefore, the expected liquid level change would be an addition of 0.1 liters of fuel to the primary reservoir 14.

Step 126: Calculate or Update Filtered Liquid Level.

From the unprocessed liquid level points, the method 100 determines a filtered block point from the sensed liquid level points over each of the computation intervals 54. While executing the method 100, the control system 30 is sensing the plurality of liquid level points during the plurality of defined computation intervals. Each defined computation interval, which may also be referred to as the interval of interest, may be defined in various ways and may be the computation interval 54 illustrated in FIG. 2. For example, the computation intervals 54 may be defined based on, and without limitation: time lapse, quantity of liquid injected into the reservoir, net quantity of liquid transferred to and from the reservoir, quantity of liquid withdrawn from the reservoir, or any other quantity that is related to actual change in liquid level. The net liquid transferred to and from the primary reservoir 14 is a parameter that is proportional to the actual liquid level change, as opposed to, for example, time, which may not be proportional to the estimated actual liquid level change. Use of the proportional parameter improves the ability of the systems and methods described herein to determine whether to make a diagnostic determination and, if necessary, to make a proper diagnostic determination.

As shown in FIG. 2, in one configuration of the method 100, the computation intervals 54 are defined by the expected change in liquid volume within the reservoir of interest, such as the primary reservoir 14. For example, and without limitation, the computation intervals 54 may be set based on every 1 liter of expected volume change, including fuel removed for the powertrain 12 and fuel added by the transfer pump 20. The computation intervals 54 may be calculated as absolute values, such that transfer in either direction completes the interval.

In an alternative configuration, the computation intervals 54 may be based on the amount of fuel withdrawn from the primary reservoir 14 for use by the powertrain 12. However, the expected liquid level change would remain calculated from both inflows and outflows of the primary reservoir 14.

From the unprocessed liquid level points, the method 100 calculates or updates the filtered block point from the sensed liquid level points over each of the computation intervals 54. Each filtered block point is a processed compilation value of all the sensed liquid level points within a computation interval, and is obtained through application of some filtering technique to all collected and sensed liquid level points. FIG. 2 shows a plurality of filtered block points 62 calculated for each of the computation intervals 54.

For example, and without limitation, the filtered block point 62 may be determined from an arithmetic mean or an exponentially-weighted moving average of the sensed liquid level points over the specific computation interval of interest. In FIG. 2, the filtered block points 62 are determined from an exponentially-weighted moving average, illustrated as the filtered level 61 of the sensed liquid level points making up the sensed level 60 for each computation interval 54.

When the filtered block point 62 is calculated, all of the sensed liquid level points contribute, such as to calculation of the arithmetic mean or exponentially-weighted moving average. However, particularly when employing arithmetic mean calculations, in order to reduce computational resources and alleviate the need to store all of the sensed liquid level points within the computation interval 54, the method 100 may use a running arithmetic mean calculation that is simply updated with each new sensed liquid level point, as illustrated by the sensed level 60. For example, the updated mean may be calculated, at loop n, as: $Mean_n = (n-1)/n * Mean_{n-1} + (1/n) * SampleValue_n$, where $Mean_{n-1}$ is the mean from the immediately preceding loop, and $SampleValue_n$ is the sensed liquid level from the current loop of the method 100.

Note that, in some configurations, different numbers of sensed liquid level points may occur during different computation intervals 54, such that some computation intervals 54 may have additional or fewer data points relative to others. This may be the case, in particular, when the computation intervals 54 are defined by net fuel transferred.

For example, when the transfer pump 20 is transferring fuel into the primary reservoir 14 while the primary pump 18 is sending fuel to the powertrain 12, these two actions have opposite effects on the net fuel transferred. Therefore, it may take longer, relative to time, for the computation intervals 54 to occur. If the sensed liquid level points are collected on a different scale, such as time, relatively more sensed liquid level points will be incorporated into the filtered block point for a longer computation interval 54.

The method 100 is tracking the number (N) of computation intervals 54, which is also the number of filtered block points 62, that have occurred since evaluation began.

Where the computation intervals 54 are time defined, N may be determined from the total time lapse divided by the size of the computation intervals 54. Therefore, N=INT (TimeLapsed/ComputationIntervalSize), where INT represents determining the integer of the resulting value. Alternatively, N may be determined in fractional values.

Where, as discussed above, the computation intervals 54 are defined by net quantity of liquid transferred to and from the primary reservoir 14, N may be determined from the expected liquid level change divided by the size of the computation intervals 54. Therefore, N=INT(ExpectedLiquidLevelChange/ComputationIntervalSize).

The expected liquid level change was determined in step 124, and may also be used for subsequent diagnostic comparisons. Therefore, the expected liquid level change is involved with both timing and diagnostics of the method 100. In configurations using time lapse for the computation intervals 54, the control system 30 will likely require the expected liquid level change to be calculated, irrespective, to be used for diagnostic comparisons. Therefore, the net-flow or expected change configuration of the computation intervals 54 alleviates the need to do time-based calculations and also liquid transfer calculations.

Step 128: Expected Liquid Level Change Increased by Computation Interval Size?

The method 100 establishes, saves, calculates, and/or captures the filtered block points 62 at the completion of each computation interval 54. Therefore, the method 100 determines, during each execution loop of the method 100, whether the expected liquid level change has increased by the computation interval size since the last filtered block point 62 was captured. This increase indicates that a complete computation interval 54 has lapsed or occurred. Alternatively stated, the method 100 is determining whether the integer of N has changed.

If a complete computation interval 54 has not lapsed or occurred, the control system 30 is not ready to store and use the filtered block point 62, and the method 100 proceeds to the end step 112 for a subsequent loop. When a complete computation interval 54 has lapsed or occurred, the method 100 proceeds to calculate its model for estimating the amount of liquid, or change in the amount of liquid, in the primary reservoir 14 based on the filtered block point.

Note that the order of the steps of the method 100 shown and described herein is not necessarily required. For example, in an alternative configuration, updating the filtered level 61, as shown in step 126, may not occur until after determining that a complete computation interval 54 has lapsed or occurred. In that configuration, processing resources may be conserved by not updating the filtered level 61. However, each of the sensed liquid level data points from loops prior to determining that a complete computation interval 54 has lapsed or occurred would need to be stored until the method 100 is ready to update the filtered liquid level.

Step 130: Capture Filtered Block Point and Increment N.

Each time that conditions are met to capture or update a filtered block point 62, the number of samples collected for the purpose of curve fitting, N, is incremented by an integer value of one. After N is incremented, execution proceeds to step 132.

When a complete computation interval 54 has lapsed or occurred, a filtered block point has been captured and N has been incremented, the method 100 moves from first block 102 to the second block 104. Note that organization of steps into the blocks is for illustration only, steps and connectors may be organized differently than shown in the figures, and steps may be moved to different blocks.

Step 132: N>Regression Sample Size?

The number of filtered block points 62 collected for the purpose of curve fitting, N, is compared to a calibrated parameter that defines the number of regression samples used to construct the regression model, such that number of filtered block points 62 are compared to a calibrated fixed number of regression samples. For example, and without limitation, based on the vehicle 10 and the control system 30, the method 100 may utilize at least six regression samples as the calibrated fixed number of regression samples. If N is greater than the calibrated fixed number of regression samples used to construct the regression model, then there are excess filtered block points 62, and the method 100 proceeds to step 133, where an outlying filtered block point 62 may be identified and discarded to make room for the most recently determined filtered block point 62.

Note that the equalities relationships described herein are illustrative of only one specific configuration. For example, configurations described herein as utilizing greater than or equal to (>=) relationships, may also simply be greater than (>) in other configurations.

Although the algorithm described herein uses a fixed number of filtered block points 62 for curve fitting, an alternative implementation may use a variable number of regression samples for curve fitting. For example, curve fitting may continue with an ever increasing number of filtered block points 62 until a diagnostic pass or fail decision is reached, or until the diagnostic enable conditions are no longer satisfied.

Alternate algorithm configurations may begin curve fitting after a calibrated minimum number of regression samples have been captured and continue to capture and curve fit additional filtered block points 62 until a calibrated maximum number of regression samples have been captured.

Step 133: Remove Outlying Filter Block Points and Update Regression Sample Arrays.

To facilitate computations, the filtered block points contributing to each regression analysis may be stored in array form. For the exemplary method described herein, an x array and a y array, both of fixed size, corresponding to the regression sample size (i.e., the calibrated fixed number of regression samples used to construct the regression model), are defined to store the x-coordinate (i.e., expected change in liquid level) and the y-coordinate (i.e., filtered block point) corresponding to each capture of a filtered block point.

If the number of filtered block points 62 collected for the purpose of curve fitting, N, is greater than the calibrated fixed number of regression samples used to construct the regression model, then the regression model residuals are calculated. After determining the residual values, the filtered block point that corresponds to the residual that has the largest absolute value is removed from the x and y arrays, and the x and y arrays are collapsed to make room for the most recently captured filtered block point 62. The current value of the expected liquid level change is then stored to array x, indexed by the calibrated fixed regression sample size, and the most recently captured filtered block point is stored to array y, indexed by the calibrated fixed number of regression samples (i.e., the regression sample size).

Following update of the x and y arrays, the method 100 proceeds to step 136. Although the algorithm described herein incorporates identifying and discarding outlying filtered block points 62, an alternative implementation may choose to use every captured filtered block point 62, in lieu of identifying and discarding outlying values.

Step 134: Update Regression Sample Arrays

If the number of filtered block points 62 collected for the purpose of curve fitting is less than or equal to the calibrated parameter that defines the number of regression samples used to construct the regression model (i.e., the calibrated fixed number of regression samples, or regression sample size), then the method 100 stores or captures the most recently determined filtered block point 62 in preparation for curve fitting. Setting or capturing the filtered block point 62 includes setting the x value to the expected liquid level change and setting the y value to the filtered liquid level.

Each time a new filtered block point 62 is captured, if the number of filtered block points 62 that have been collected for the purpose of curve fitting, N, is less than or equal to the calibrated fixed number of regression samples used to construct the regression model, then the regression arrays are updated without the need to identify and remove outlying samples. The current value of the expected liquid level change (determined in step 124) is stored to an array x, indexed by N, and the most recently captured filtered block point 62 is stored to an array y, indexed by N, such that: x[N]=ExpectedLiquidLevelChange; and y[N]=FilteredLiquidLevel.

Following update of the x and y arrays, execution proceeds to step 135. Alternate algorithms may be implemented in a manner that does not require the storage of each filtered block point 62 and the corresponding value for expected liquid level change to arrays, but instead employs a set of running calculations to determine the curve fit statistics and parameters of interest.

Step 135: N=Regression Sample Size?

If the number of filtered block points 62 collected for the purpose of curve fitting is less than the calibrated parameter that defines the number of regression samples used to construct the regression model (i.e., the calibrated fixed number of regression samples), then the method 100 proceeds to the end step 112 for a subsequent loop. For example, depending on the vehicle 10 and the control system 30, the method 100 may utilize at least of six regression samples.

Step 136: Calculate Curve Fit and Regression Statistics from Filtered Block Points.

If the number of filtered block points collected for the purpose of curve fitting, N, is greater than or equal to the calibrated fixed number of regression samples used to construct the regression model, then the method 100 proceeds to step 136. From the filtered block points 62 determined by the control system 30, the method 100 determines a curve fit through regression analysis.

In the example shown in FIG. 2, the regression is a linear curve fit. However, higher order curve fits may also be applied, although additional computational resources may be required for non-linear curve fit calculations. For example, and without limitation, the method 100 may employ an ordinary least squares (OLS) curve fitting method to the determined filtered block points 62 to determine the regression line 70. In one configuration, the filtered block points 62, which occur along the filtered level 61, may be the exponentially weighted moving average of the sensed liquid level points that form the sensed level 60, during each computation interval 54.

Note that the OLS regression is performed on the filtered block points 62, not on the sensed liquid level points of the computation interval 54 and not on the sensed liquid level points of the entire sensed level 60. The OLS regression of the filtered block points 62 is calculated as function of the expected liquid level change.

As part of the regression curve fit, the method 100 calculates several coefficients and statistics. For example, and without limitation, the method 100 may calculate: slope, standard error of regression (SER), and intercept.

If the OLS regression is being performed over a discrete window—where a new result is provided after every set of N filtered block points 62 have been captured—then determination of the OLS regression parameters and statistics can be can be implemented as a running calculation (i.e., without the need to store each of the N filtered block points 62). However, if the OLS regression is configured to identity and discard outlying samples, or is being performed over a running window—where once a calibrated fixed number of regression samples have been collected, a new result is provided upon completion of each subsequent computation interval 54, with the oldest filtered block point 62 being discarded and the newest filtered block point 62 being added to the OLS regression—then provisions must be made to store, in memory of the control system 30, all samples that contribute to determination of the OLS regression parameters and statistics.

Step 138: Determine Actual Liquid Level or Liquid Level Change.

From the regression analysis, the method 100 determines an estimate for the actual liquid level or the actual liquid level change. These levels are estimates based on the regression analysis from the filtered block points 62.

The basic equation for estimating the actual liquid level is y=mx+b, and the basic equation for estimating the change in actual liquid level is $\Delta y = m(\Delta x)$, where m is the slope, x is the parameter used to define the computation interval and b is the intercept. These formulae work irrespective of the how the computation intervals 54 are defined.

In the example shown in FIG. 2, where the computation intervals 54 are defined based on expected change in liquid level, the estimated change in actual liquid level may be expressed as:

$$\text{ActualLiquidLevelChange} = \text{Slope} * (x[\text{RegressionModelSampleSize}] - x[1]).$$

The term x[RegressionModelSampleSize] is the value of x corresponding to the most recently captured filtered block point 62 that contributes to the current regression analysis, and the term x[1] is the value of x corresponding to the first (i.e., oldest) filtered block point 62 that contributes to the current regression analysis. In example illustrated by FIG. 2, the actual liquid level change is approximately 10.4 L, as shown by the actual level change 72, such that the determined actual liquid level is approximately 63.4 L. Note that the change is relative to the first filtered block point 62 that contributes to the current regression analysis, which, in the example of FIG. 2, occurs at 1 L of liquid transferred along the x-axis 52 and approximately 53 L of total fuel along the y-axis 56.

Although the algorithm described herein is concerned with determination of an estimate for the change in actual liquid level, alternative implementations may require an estimate for the actual liquid level. In such configurations, the method 100 may be modified to add (or subtract) the determined change from the starting actual liquid level or the starting expected liquid level to determine an estimate of the actual liquid level.

The estimate for actual liquid level may be reported or signaled in order to alert the operator of the vehicle 10 to the determined level. For example, a signal may be sent by the control system 30 to be displayed on an instrument panel and used by other systems. Furthermore, the estimate for actual liquid level may be used to enhance liquid level display, such as using the sensed liquid level for display purposes when a vehicle is stationary, and using the estimate for actual liquid level determined by the method 100 during periods of vehicle motion.

At this point, the method 100 has calculated its estimate of the actual liquid level change and has calculated the expected liquid level change. Therefore, the method 100 may include calculating a potential level error. This potential level error may be the difference between the expected liquid level, or change, and the actual liquid level, or change.

From the potential level error, a simple diagnostic determination could be made by comparing the potential level error to a calibrated threshold. For example, if the potential level error is greater than the calibrated threshold, the system would fail the diagnostic, and if the potential level error is less than or equal to the calibrated threshold, the system would pass the diagnostic. The potential level error may also be compared to more complex thresholds, as described herein.

However, the method 100 is determining an estimate of the actual liquid level change, as opposed to an absolute determination. Therefore, the method 100 also determines whether the calculated estimate of the actual liquid level change is sufficiently accurate, before diagnosing whether the liquid systems are likely functioning properly.

Step 140: Calculate Confidence Ratio.

The method 100 calculates or determines a confidence ratio from the standard error of regression of the fitted curve determined from the filtered block points 62, which was determined as part of the regression analysis in step 136. The standard error of regression represents the standard deviation of the filtered block point 62 computations about the OLS regression prediction. That is, the standard error of regression is a measure of how well the regression model fits all of the filtered block point 62 computations that contributed to determination of the regression model.

The confidence ratio may be calculated as follows:

Confidence Ratio=($x$[Regression sample Size]−$x$[1])/ SER.

In general, a large value of the confidence ratio indicates that the expected change in liquid level is large relative to the prediction variation of the regression model, such that relatively higher confidence ratios suggest data that is relatively better suited to evaluating the functional performance of components or systems under diagnosis.

Step 142: Confidence Ratio>Minimum Confidence Ratio?

The method 100 next determines whether the estimated actual liquid level change provided by the regression model is sufficient to use for diagnostic purposes. If the actual liquid level change and the expected liquid level change are greatly different, it may suggest a fault in some system of the vehicle 10. For example, and without limitation, the powertrain 12 may be drawing too much or too little fuel from the primary reservoir 14; the transfer pump 20 may not, in spite of commands, be transferring fuel to the primary reservoir 14; or the primary sensor 32 may not be responding properly to actual changes in fuel level.

If such errors are, in fact, occurring, the control system 30 may be configured to alert the operator, such as via a warning light or a diagnostic message sent via a network connection (such as email or communication with a mobile app). However, it may be preferable that the method 100 withholds such warnings if either the errors are not, in fact, occurring or the control system 30 determines that it cannot confirm that errors are occurring.

After calculating the confidence ratio, the method 100 includes comparing the determined confidence ratio to a minimum confidence ratio. In general, the minimum confidence ratio is a calibrated value that is chosen in a manner to ensure that the expected liquid level change is sufficiently large in relation to the variation inherent in the estimate for actual liquid level change before proceeding with a diagnostic determination. The exact value of the minimum confidence ratio may be specific to the vehicle 10.

If the determined confidence ratio is less than or equal to the minimum confidence ratio, the method 100 will make no diagnostic determination, irrespective of the size of the potential level error between the expected liquid level change and the estimated actual liquid level change, and the method 100 proceeds to the end step 112. If the determined confidence ratio is greater than the minimum confidence ratio, the method 100 will make a diagnostic determination from the potential level error.

In the example illustrated in FIG. 2, curve fitting was first executed when the expected change in primary liquid volume reached 6.0 L, after the first six filtered block points 62 were captured. Due to the impact of disturbances on the sensed level 60 between approximately 4.5 L and 6.5 L of expected change in primary liquid volume, which translated in to a relatively high standard error of estimate (SER), the resultant calculation for confidence ratio was approximately 5.4.

However, for the vehicle 10 and the control system 30, the minimum confidence ratio was pre-calibrated at 8. Therefore, in this instance, the method 100 would have proceeded to the end/loop step 112, and would have skipped making any (positive or negative) diagnostic determination. By using the confidence ratio to determine whether a diagnostic determination can, or should, be made, the method 100 improves diagnostic abilities of the vehicle 10 and control system 30.

Still with reference to FIG. 2, curve fitting was executed for a second time when the expected change in primary liquid volume reached 7.0 L, after the seventh filtered block point 62 was captured. In this case, the outlier point 64 was identified and discarded and the regression model was updated with the newly captured seventh filtered block point 62.

The removal of the outlier point 64, and subsequent compression of the arrays to accommodate a new filtered block point sample, is illustrated by step 133. As a consequence of discarding the outlying sample from the outlier point 64, and incorporating a new filtered block point sample, the standard error of estimate (SER) for the regression model decreased, and the resultant calculation for confidence ratio was approximately 11.7. Therefore, because the minimum confidence ratio was pre-calibrated at 8 for the vehicle 10 and the control system 30, after the second regression, the method 100 would have proceeded to step 144 to make a diagnostic determination.

Step 144: Determine Actual Liquid Level Error Max.

After establishing that the collected data and the regression are sufficient for a diagnostic determination, the method 100 then proceeds to determine the maximum measurement errors inherent in the expected liquid level change and in the estimate of the actual liquid level change. The actual method used to arrive at the maximum error values may vary depending on the nature of the signals, sensors, and processors used.

The maximum measurement error inherent in the estimate of the actual liquid level change may be due to, for example and without limitation, sampling or conversion variations associated with sensed level 60. In the configuration shown in FIG. 1, the linear nature of the primary sensor 32 and float 34 relative to the non-linear volume of the primary reservoir 14 may result in conversion variation, in addition to other variations. Note that the standard error of regression (SER), as determined from the regression model, is considered separately, such that the SER does not factor into determination of the measurement error at this step.

Step 146: Determine Expected Liquid Level Error Max.

The maximum measurement error inherent in the expected liquid level change may be due to, for example and without limitation, inaccuracies in sensed, estimated, or reported flow rates to and from the primary reservoir 14 (or other reservoir of interest). In the configuration shown in FIG. 1, both the primary pump 18 and the transfer pump 20 are transferring liquids and there may, therefore, be errors inherent in the respective flow rate determinations.

For one-sided tests (e.g., checking for a change in liquid level greater than a minimum threshold), these sources of uncertainty can be included as part of the computation of the expected liquid level change, such as in step 124, and as was done for the example illustrated in FIG. 2. Additionally, steps 144 and 146 may be considered a single step of determining inherent errors.

Step 148: Calculate Total Variation.

The method 100 calculates a total measurement and estimation variation, which may be referred to simply as the total variation. Note that other error types may be incorporated into the determination of the total variation.

The total variation is used to determine where the diagnostic fail threshold, or thresholds, is to be positioned relative to the expected liquid level change. The total variation may be calculated based on, at least, the maximum measurement and estimation errors calculated in steps 144 and 146, the standard error of regression, and a calibrated multiplier applied to the standard error of regression.

Therefore, the total variation may be determined by the formula:

TotalVariation=EstimatedLiquidLevelErrMax+ExpectedLiquidLevelErrMax+ (StandardErrorOfRegression*SERMultiplier).

Note that other factors may be included in the calculation of the total variation, and that the SER multiplier may be calibrated differently for different implementations of the method 100 or based on the vehicle 10 and the control system 30.

Step 150: Determine Upper Failure Threshold.

From the total variation, the method 100 calculates a threshold range of allowable variation for use in the diagnostic determination. In the exemplary configuration, there are both upper and lower thresholds. However, some configurations may be one-directional and have only a single threshold.

For the upper failure threshold, the method 100 uses the following formula:

UpperFailureThreshold=ExpectedLiquidLevelChange+TotalVariation.

Step 152: Determine Lower Failure Threshold.

For the lower failure threshold, the method 100 uses the following formula:

LowerFailureThreshold=ExpectedLiquidLevelChange−TotalVariation.

Note that the upper and lower thresholds in the configuration shown are symmetric about the expected liquid level change. However, in other configurations of the method 100, they may be asymmetric, such that, for example, there may be a larger acceptable range for the upper threshold.

Furthermore, some configurations may include only a single direction of failure threshold. For example, if the method 100 were configured only to confirm that the transfer pump 20 is operating, there may be only a minimum threshold to diagnose that liquids are being successfully transferred from the secondary reservoir 16 to the primary reservoir 14.

By using the SER to determine the total variation, and subsequently the upper and lower thresholds, the method 100 is incorporating its own data into the diagnostic determination. In an alternate configuration, the upper and lower thresholds may be based on pre-calibrated values. However, the method 100 improves the diagnostic by directly accounting for measurement variation in determination of the diagnostic pass and fail thresholds.

Step 154: Actual Liquid Level Change within Threshold Range?

The method 100 compares the actual liquid level change, calculated in step 138 to the failure thresholds. In an alternative system, the method 100 may simply use calibrated threshold ranges and the potential level error (i.e., the difference between the actual liquid level change and the expected liquid level change) to make the diagnostic determination.

However, in the configuration shown, the method 100 also factors the calculated total variation into this comparison, by establishing the upper and lower failure thresholds in steps 150 and 152. Using the total variation incorporates measurement and sensing errors into the diagnostic failure determination, as opposed to comparing the potential level error (a simple mathematical difference between the actual and expected values) to a calibrated value, or values.

Therefore, in the comparison of step 154, the method 100 determines whether the actual liquid level change is either greater than the upper failure threshold or is less than the lower failure threshold. Mathematically, the threshold determination may be expressed as:

(ActualLiquidLevelChange>UpperFailureThreshold) OR (ActualLiquidLevelChange<LowerFailureThreshold)?

In the example illustrated in FIG. 2, the calculated actual liquid level change was approximately 10.4 L and, as discussed previously, the expected liquid level change was 6.0 L. The total variation was determined to be approximately 2.6 L, such that the upper failure threshold was 8.6 L and the lower failure threshold was 3.4 L.

Therefore, on the second regression analysis, determined after the seventh filtered block point 62, the method 100 determined both that the confidence ratio was sufficient to make a diagnostic determination and that the estimated actual liquid level was outside of the threshold range (i.e., it was greater than the upper failure threshold). Note that other configurations of the method 100 may only apply a one-sided test. For example, to diagnose whether the transfer pump 20 is properly operating, the method 100 may only determine whether the actual liquid level change is greater than the lower failure threshold. In such a configuration, the example illustrated in FIG. 2 would have passed the diagnostic, as the determined actual liquid level change (10.4 L) was greater than lower failure threshold (3.4 L), which suggests that the transfer pump 20 is moving fuel from the secondary reservoir 16 to the primary reservoir 14.

Alternatively stated, the method 100 is comparing the magnitude of the potential level error, which is the difference between the estimate actual liquid level change and the expected liquid level change, to the total variation. Comparison between the magnitude of the potential level error and the total variation works when the test is symmetric, but other configurations may use asymmetric, or one-sided, comparisons that differ based on the direction of the potential level error.

Step 156: Record or Report Test Pass.

Where the actual liquid level change is within the diagnostic threshold range, the method proceeds from step 154 to report or record that the system has passed the diagnostic determination.

This information may be stored, may be used by other systems, or may be used as part of a larger diagnostic algorithm for determining the correct function of a component or system. For example, a test result for the primary sensor 32 may be used in combination with a test result for the secondary sensor 36 to diagnose the overall performance of transfer pump 20 as well as the individual performance of the primary sensor 32 and secondary sensor 36.

Step 158: Record or Report Test Failure.

Where the actual liquid level change is outside of the diagnostic threshold range, the method proceeds from step 154 to report or record that the system has failed the diagnostic determination. This information may be stored or may be used by other systems. In the example shown in FIG. 2, and discussed above, the method 100 made a negative diagnostic determination.

The diagnostic failure may trigger warning lights or signals, and may be used to adjust operation of other systems. Additionally, the diagnostic failure may be used as part of a larger diagnostic algorithm for determining the correct function of a component or system, such as a test result for the primary sensor 32 used in combination with a test result for secondary sensor 36 to diagnose the overall performance of transfer pump 20 as well as the individual performance of the primary sensor 32 and the secondary sensor 36.

Step 160: Reset Diagnostic Parameters.

Following a diagnostic pass or fail report, the method 100 proceeds to reset the diagnostic parameters. The diagnostic parameters are also reset if it is the first time through the loop after enable conditions are satisfied, as redirected from determination step 122.

The diagnostic parameters reset are, at least: N=0, and expected liquid level change=0. Note that resetting the expected liquid level change also effectively resets the estimate for the actual liquid level change. The method 100 then loops, repeats, or waits until called upon for further determination of the relevant liquid levels.

The detailed description and the drawings or figures are supportive and descriptive of the subject matter discussed herein. While some of the best modes and other embodiments have been described in detail, various alternative designs, configurations, and embodiments exist.

The invention claimed is:

1. A method for determining a liquid level change of a reservoir subject to disturbances, the method comprising:
   sensing a plurality of liquid level points during a plurality of defined computation intervals;
   determining a plurality of filtered block points from the sensed liquid level points occurring during each of the computation intervals;
   fitting a regression model to the determined filtered block points, including determining a slope and a standard error of regression; and
   determining an actual liquid level change from the slope of the regression model.

2. The method of claim 1, further comprising:
   monitoring an inflow and an outflow from the reservoir;
   determining an expected liquid level change from the inflow and the outflow;
   calculating a potential level error from the difference between the expected liquid level change and the actual liquid level change;
   determining a confidence ratio from the standard error of regression of the regression model; and
   comparing the determined confidence ratio to a minimum confidence ratio:
      if the determined confidence ratio is higher than the minimum confidence ratio, making a diagnostic determination from the potential level error; and
      if the determined confidence ratio is lower than the minimum confidence ratio, making no diagnostic determination, irrespective of the potential level error.

3. The method of claim 2, wherein the computation intervals are defined by a parameter that is proportional to the actual liquid level change.

4. The method of claim 2, wherein the computation intervals are defined by net liquid transferred to and from the reservoir.

5. The method of claim 2, wherein the filtered block points are calculated as an arithmetic mean of the sensed liquid level points over each of the computation intervals.

6. The method of claim 2, wherein the filtered block points are calculated as an exponentially weighted moving average of the sensed liquid level points over each of the computation intervals.

7. The method of claim 2, wherein the regression model is an ordinary least squares (OLS) model.

8. The method of claim 2, wherein, if the determined confidence ratio is higher than the minimum confidence ratio, making the diagnostic determination includes:
   determining a total variation from at least the standard error of regression multiplied by a calibrated factor;
   determining a lower failure threshold by subtracting the total variation from the expected liquid level change; and
   comparing the actual liquid level change to the lower failure threshold:
      if the actual liquid level change is less than the lower failure threshold, recording a diagnostic failure; and
      if the actual liquid level change is greater than the lower failure threshold, recording a diagnostic pass.

9. The method of claim 8, wherein making the diagnostic determination further includes:
   determining an upper failure threshold by adding the total variation to the expected liquid level change; and
   comparing the actual liquid level change to the upper failure threshold:
      if the actual liquid level change is greater than the upper failure threshold, recording a diagnostic failure; and
      if the actual liquid level change is greater than the lower failure threshold and less than the upper failure threshold, recording a diagnostic pass.

10. The method of claim 9,
    wherein the computation intervals are defined by a parameter that is proportional to the actual liquid level change; and
    wherein the regression model is a linear model.

11. The method of claim 10, further comprising:
    comparing the number of the filtered block points to a minimum regression sample size; and
    determining the confidence ratio only if the number of the number of the filtered block points is greater than or equal to the minimum regression sample size.

12. A method for determining a liquid level of a reservoir subject to disturbances, the method comprising:
    sensing a plurality of liquid level points during a plurality of defined computation intervals;
    determining a plurality of filtered block points from the sensed liquid level points occurring during each of the computation intervals;
    fitting a regression model to the determined filtered block points, including determining a slope and a standard error of regression; and
    determining an actual liquid level from the slope of the regression model.

13. The method of claim 12, further comprising:
    monitoring an inflow and an outflow from the reservoir;
    determining an expected liquid level from the inflow and the outflow;

calculating a potential level error from the difference between the expected liquid level and the actual liquid level;

determining a confidence ratio from the standard error of regression of the regression model; and comparing the determined confidence ratio to a minimum confidence ratio:
- if the determined confidence ratio is higher than the minimum confidence ratio, making a diagnostic determination from the potential level error; and
- if the determined confidence ratio is lower than the minimum confidence ratio, making no diagnostic determination, irrespective of the potential level error.

14. The method of claim 13, wherein, if the determined confidence ratio is higher than the minimum confidence ratio, making the diagnostic determination includes:

determining a total variation from at least the standard error of regression multiplied by a calibrated factor;

determining a lower failure threshold by subtracting the total variation from the expected liquid level; and comparing the actual liquid level to the lower failure threshold:
- if the actual liquid level is less than the lower failure threshold, recording a diagnostic failure; and
- if the actual liquid level is greater than the lower failure threshold, recording a diagnostic pass.

15. The method of claim 14,
wherein the computation intervals are defined by a parameter that is proportional to the actual liquid level; and
wherein the regression model is a linear model.

16. The method of claim 15, wherein the regression model is an ordinary least squares (OLS) model.

* * * * *